United States Patent [19]
Ikezawa et al.

[11] 4,421,787
[45] Dec. 20, 1983

[54] PROCESS FOR FORMING A THIN DENSE SINTERED LAYER

[75] Inventors: Kenji Ikezawa, Yokohama; Hiroshi Takao, Kamakura; Hiroyuki Aoki, Noba; Shinji Kimura, Yokohama, all of Japan

[73] Assignee: Nissan Motor Company, Limited, Yokohama, Japan

[21] Appl. No.: 263,558

[22] Filed: May 14, 1981

Related U.S. Application Data

[63] Continuation of Ser. No. 58,428, Jul. 19, 1979, abandoned.

[30] Foreign Application Priority Data

Jul. 24, 1978 [JP] Japan ................. 53-089322

[51] Int. Cl.³ ............................................. B05D 5/12
[52] U.S. Cl. ................. 427/126.2; 427/126.3; 427/376.2; 427/380; 204/421
[58] Field of Search ................. 204/195 S; 427/126.2, 427/126.3, 123, 125, 376.1, 376.2, 376.3, 376.6, 376.8, 379, 380, 383.1, 383.3, 383.5, 404, 419.1, 419.2, 419.3, 419.4, 419.6, 419.7

[56] References Cited

U.S. PATENT DOCUMENTS

| 2,987,423 | 6/1961 | Sternberg . | |
| 3,397,076 | 8/1968 | Little | 427/379 |
| 3,634,113 | 1/1972 | Fehrenbacher | 429/33 |
| 3,635,759 | 1/1972 | Howatt | 427/376.2 |
| 3,754,968 | 8/1973 | Reznik . | |
| 4,074,010 | 2/1978 | Knight | 427/376.2 |
| 4,107,019 | 8/1978 | Takao et al. | 204/195 S |
| 4,107,348 | 8/1978 | Hirschhorn | 427/419.4 |

FOREIGN PATENT DOCUMENTS 2742278 3/1978 Fed. Rep. of Germany .
2746381 4/1978 Fed. Rep. of Germany .

Primary Examiner—Norman Morgenstern
Assistant Examiner—Richard Bueker
Attorney, Agent, or Firm—Schwartz, Jeffery, Schwaab, Mack, Blumenthal & Koch

[57] ABSTRACT

A process for forming a thin dense layer from a paste of powder in organic vehicle, comprises applying the paste onto a substrate by a screen printing technique, drying and sintering the applied paste under sintering conditions, and repeating the above procedure at least one more time, so as to yield a thin dense sintered layer which is longer in liftetime and more stable in quality than those obtained by known techniques.

8 Claims, 4 Drawing Figures

PROCESS FOR FORMING A THIN DENSE SINTERED LAYER

This is a continuation, of application Ser. No. 058,428, filed July 19, 1979, now abandoned.

This invention relates to a process for forming a dense thin sintered layer, and more particularly to an improved screen printing process for forming a dense thin sintered layer from pastes such as of oxygen ion conductive solid electrolyte, alumina or glass insulators, and conductive metals in the form of powder dispersed in organic vehicle.

It is an object of the present invention to provide a process for forming a thin sintered layer which is more dense than as is obtained by a known screen printing method.

It is another object of the present invention to provide an improved screen printing process which can yield a satisfactorily thin dense sintered layer without involving any severe controls of operating conditions such as viscosity of paste, powder/vehicle ratio, printing and drying conditions as will be required in the prior art screen printing method.

It is a further object of the present invention to provide a process as mentioned above, which can yield a thin dense sintered layer from paste compositions which is longer in lifetime and more stable in quality than those obtained by the known screen printing method.

The above and other objects, features and advantages of the invention will become apparent from the following description and the appended claims, taken in conjunction with the accompanying drawings, in which:

Figure 3:
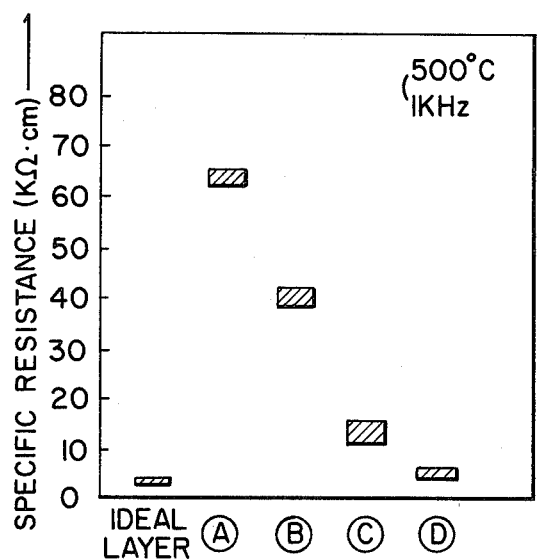
Figure 4:
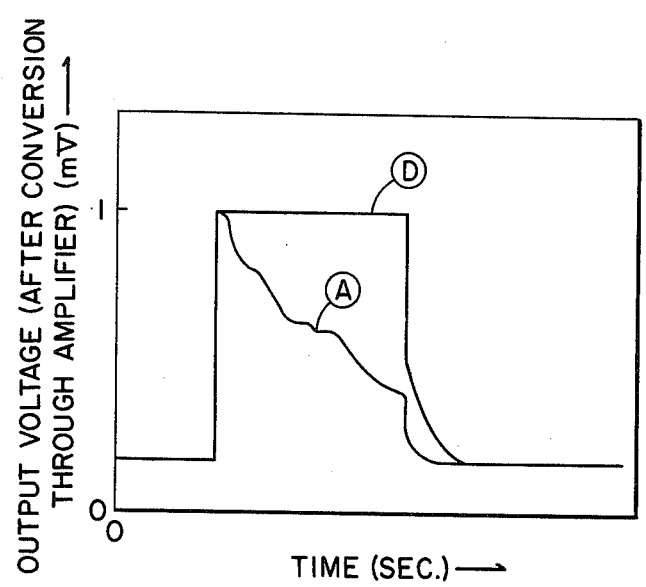

FIG. 3 is a graphical representation of specific resistance of the solid electrolyte layers obtained by the prior art procedures A and B and also by the procedures C and D of the invention; and FIG. 4 is a graphical representation of an output characteristic of each of oxygen sensors which are, respectively, provided with the thin solid electrolyte layers formed according to the prior art procedure A and the procedure D of the present invention.

As typical of such thin layer formation techniques using paste compositions, there is well known a screen printing process. The screen printing process is used in various fields, particularly widely in the field of electronic or electric industries. In this process, pastes of powder of desired nature dispersed in organic vehicle are first provided and are then printed on suitable substrate by the screen printing technique, dried at suitable temperature and finally sintered at elevated temperature to form a thin sintered layer on the substrate. The formation of a thin solid layer is necessitated in other various industries including automotive industry. For example, much attention has been recently directed to an oxygen sensor in the automotive industry. The oxygen sensor makes use of an oxygen ion conductive solid electrolyte layer, which is preferred to be as thin and dense as possible for the reason which will be discussed in detail hereinlater.

The solid electrolyte layer has been heretofore formed by several methods including a plasma spray coating method, a high frequency spattering method and the like. However, these methods are not satisfactory in providing a thin dense layer of such electrolyte. There has been proposed in Japanese Patent Application No. 53-58280 a paste composition of oxygen ion conductive solid electrolyte in organic vehicle which is particularly adaptable for use with the screen printing technique.

As is well known, the electromotive force of an oxygen concentration cell or an oxygen sensor constructed on the basis of the principle of the cell decreases with an increase of the internal resistance of the cell or sensor. In order to produce the electromotive force stably and as largely as possible, it is necessary to reduce the internal resistance of the cell or sensor to a minimum. The internal resistance of the cell or sensor is substantially dependent on the resistance of a solid electrolyte used.

The resistivity of a solid electrolyte is expressed as a function of the absolute temperature and exponentially decreases with an increased temperature. Now assuming that a solid electrolyte is applied as an oxygen sensor of controlling the air-fuel ratio of a combustion system such as of an automotive engines, the output potential from the sensor should be at a level required for controlling the combustion system at temperatures above about 300° C. In order to control the air-fuel ratio at the time of cold start, the sensor must normally operate even at temperatures as low as one hundred and several tens centrigrade. To satisfy the above reqirements by the use of existing solid electrolytes, the sensor must be of a specific type. That is, the solid electrolyte layer of the sensor is made very thin so that the internal resistance of the sensor itself becomes small, permitting a loss of the electromotive force due to the internal resistance to be reduced to a minimum. This presents advantages that the electromotive force increases because of the reduction of the loss and that the response speed of the sensor is improved.

The above is more particularly illustrated by way of an oxygen sensor for air-fuel ratio control using a thin or superposed layer of oxygen ion conductive solid electrolyte. The sensor is schematically shown in FIG. 1, in which indicated at 1 is an alumina insulating substrate, at 2 is a platinum electrode vacuum-deposited on the substrate 1, at 3 is a reference oxygen partial pressure producing Ni-NiO electrode vacuum-deposited on the platinum electrode 2, at 4 is a solid electrolyte which is obtained by printing a solid electrolyte paste composition by a screen printing method to surround the electrode 3 and sintering the applied paste, and at 5 is a platinum electrode vacuum-deposited on the solid electrolyte layer 4.

Figure 1:
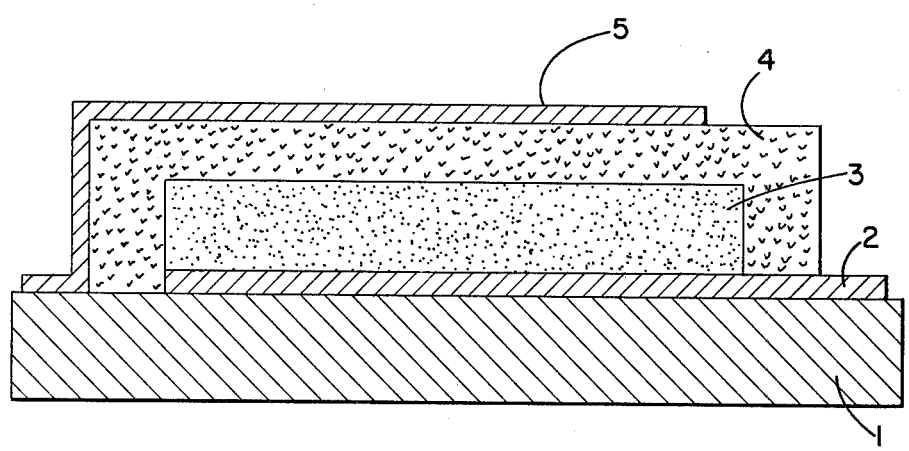
FIG. 1 is a schematical sectional view of a typical oxygen sensor, as illustrated hereinbefore, using a thin layer of solid electrolyte.

The theoretical electromotive force of the oxygen sensor shown in FIG. 1 is represented by the following equation using a ratio of oxygen partial pressures at opposite sides of the solid electrolyte layer 4:

$$E = \frac{RT}{4F} \ln \frac{PO_2}{PO'_2}$$

in which R represents a gas constant, F is a Faraday's constant, T represents an absolute temperature, $PO_2$ represents a reference oxygen partial pressure which is determined from an equilibrium oxygen partial pressure between the metal and the metal oxide, i.e. Ni-NiO, to be the reference oxygen artial pressure generating substance in the form of a layer which is provided on the inner side of the electrolyte layer 4, and $PO'_2$ represents an oxygen partial pressure in the exhaust gas at outer side of the solid electrolyte layer 4.

It has been confirmed experimentally that the solid electrolyte layer should meet the following requirements to permit the oxygen sensor to operate stably.

(1) The layer is so dense as not to allow gas permeation.
(2) The layer is stable in composition without undergoing any significant change after a lapse of time.
(3) The layer shows great conductivity.

Of these, the requirement (1) where the layer is dense and passes no gas therethrough is most important. If an exterior atmospheric gas readily passes through the solid electrolyte layer, the electromotive force E becomes zero. Even though the gas permeation through the layer is very small, the output potential E from the sensor will gradually decrease as it has been used long and finally come to zero.

Accordingly, careful attention should be paid to the formation of the thin solid layer so that the layer is do dense as to permit no gas permeation. However, it has been experimentally found that the yield of a gas-permeation-free, dense layers of solid electrolyte by a known screen printing method is as low as about 50% mainly due to great variations in a number of operating factors which will be inevitably involved during the course of fabrication of the sensor.

Typical factors which will adversely affect the denseness of the layers are:

(1) Inhomogeneous dispersion of powder in paste.
(2) Changes in properties of the paste, e.g. viscosity and powder/vehicle ratio, with a lapse of time.
(3) Variations in printing thickness and other printing conditions.
(4) Variation in drying conditions.

In order to form a dense layer, all the adversely affecting factors must be removed by severely controlling all the consitions relating to such factors. However, difficulties will be encountered in such severe control of the conditions within desired ranges so as to attain the denseness of the layer. Variations of such conditions to certain extent will be inevitably involved in an industrial practice.

As will be described hereinabove, formation of a very thin dense solid electrolyte by the prior art screen printing method involved severe controls such as in preparation and storage of the paste, printing and drying conditions and the like, resulting in lowering of productivity.

According to the present invention, there is provided a process for forming a thin dense solid layer from a paste composition which comprises a series of steps of applying a paste of a solid powder in organic vehicle onto a substrate by a screen printing technique, drying and sintering the applied paste under sintering conditions and repeating the above procedure at least one more time.

Preferably, each sintering prior to a series of the final coating, drying and sintering steps is carried out at temperatures 0.4-0.8 times as low as a final sintering temperature which may vary depending on the type of paste.

Also, it is preferred that the powder in a paste applied in the final series of steps has an average size of below 0.9 times as small as that used prior to the final procedure.

The present invention is, as described hereinbefore, characterized in that a series of paste coating, drying and sintering steps is repeated at least two times. Now assuming that the series of the steps is repeated x times, the layer obtained after completion of the (x-1)th sintering step may still contain imperfections or pores which permit the possible gas permeation as discussed hereinbefore. In order to remove the imperfections, an xth paste coating is conducted to allow the powder in the paste to be charged in the imperfections (or pores) present in the layer by the use of the fluidity of paste. Needless to say, the reason why the gas permeation takes place is due to the presence of open pores in the layer. These open pores are almost completely charged and filled with the powder in the final coating application.

In order to further improve the denseness of the layer, it has been experimentally found and, in fact, is preferred that each sintering up to the (x-1)th series of the steps is conducted at a temperature as low as 0.4-0.8 times of the final sintering temperature. This is because the layer which has been calcined at such low temperature remains porous, which facilitates the powder of the paste to be more densely charged in the pores in a final (xth) coating step due to the fluidity of the paste and to the absorptibity of the porous layer.

In view of the above fact, it is preferred that the powder of the paste used in the final xth series has an average size smaller than that used prior to the final coating step. In general, it is believed that the average size of the pores present in the calcined layer formed during the course of up to the (x-1)th series of the procedures is smaller than an average size of the powder due to its self-charging action and as a result of calcination. According, in order that the pores in the layer are satisfactorily charged with the powder in the final coating procedure, it is preferred that the average size of the powder in the paste used in the final coating procedure is smaller than that of the powder employed prior to the final series. Though the average size of the powder used in the final coating procedure may more or less vary depending on the average size of the powder employed prior to the final step and the calcining temperature, it has been experimentally confirmed that the average size of powder used in the final coating procedure is desired to be not greater than 0.9 times that of powder used prior to the final procedure.

As mentioned hereinabove, the calcining temperature is preferred to be 0.4-0.8 times as low as a final sintering temperature for the reason that a porous layer is purposely formed to allow fine powder to be readily charged in the pores in a final coating step. When the calcination is carried out at temperatures outside the above-indicated range, e.g. at higher temperatures than as indicated, the coating layer becomes too dense, producing similar results in a case where a series of coating and sintering steps is simply repeated. On the other hand, if the calcination is conducted at temperatures lower than those in the defined range, the layer becomes satisfactorily porous but remains small in strength, imposing limitations on subsequent handling and coating operations, coupled with another disadvantage that the organic vehicle in the paste is not completely dissipated or decomposed and remains in the layer.

The concept of the present invention has been described above and the present invention will be more particularly illustrated.

The process of the present invention is adaptable for application to various types of solid powder-containing pastes. The application to a solid electrolyte paste will be particularly described.

As mentioned, there has been proposed in Japanese Patent Application No. 53-58280 a solid electrolyte paste composition. Briefly, the paste composition comprises an oxygen ion conductive solid electrolyte in the form of a powder and an organic vehicle dispersing the powder therein. The powder and the vehicle are mixed in a weight ratio of 1:0.25-2.5. The powder is severely controlled to have an average size not greater than $0.7\mu$, maximum size not greater than $6.0\mu$, and a specific surface area within a defined range. This paste composition is designed to be applied by a known screen printing method so as to form a thin dense solid electrolyte layer. The paste composition is applied onto an insulating substrate by a screen printing technique, dried at 100°–200° C., and sintered at 800°–1500° C. to form a solid electrolyte layer.

According to the process of the invention, however, it is not necessary to powder the solid electrolyte to such a fine extent in order to give a dense thin layer in high yield. In the practice of the invention, an average size of the powder is generally in the range of $0.2\mu$ to $12\mu$, preferably $0.5\mu$ to $8\mu$. Such larger-sized powder will suffice to give a dense layer. With respect to the maximum size of the powder, it is necessary that the maximum size is $40\mu$ or less, because a paste containing the powder is printed or applied onto a substrate by a screen printing technique. Such size of powder can be in practice selected using a 400 mesh sieve.

When the powder used prior to a final coating procedure is controlled to have its size within the above-defined range, the size of powder used in the final coating procedure is preferred to be not greater than 0.9 times as small as the initially employed one.

The solid electrolyte useful in the invention are those which are known to the art include, for example, $Y_2O_3$-$ZrO_2$, $CaO$-$ZrO_2$, $ThO_2$-$Y_2O_3$, $NbO_2$-$Bi_2O_3$, $CeO_2$-$La_2O_3$ and the like.

The organic vehicle is a mixture of an organic binder and a high boiling organic solvent and, if necessary, additives. The organic binder is, for example, a cellulose derivative such as methyl cellulose or nitro cellulose orginarily employed in various types of paste compositions to be applied by the known screen printing method. The high boiling solvent is, for example, terpineol or cyclohexane. Plasticizers such as dibutyl phthalate or surfactants such as polyethylene glycol ether may be added as additives, if necessary.

The powder and the organic vehicle are mixed well in a mill such as a roller mill, a vibrating mill, a rotary ball mill or the like to give the paste.

The solid electrolyte paste suitable for the practice of the invention has a solid content of 30% to 70% on the weight basis. The organic vehicle comprises 2.0 wt% to 15.0 wt% of the binder, 45.0 wt% 80.0 wt% of the high boiling solvent, 10 wt% to 40 wt% of the plasticizer, and 1.0 wt% to 3.5 wt% of the surfactant, when the vehicle is 100%.

The paste is readily prepared by mixing the powder and the organic vehicle in a mill such as a roller mill, a vibrating mill, a rotary ball mill or the like.

The solid electrolyte paste thus prepared is ready for application and when, for example, applied as an oxygen sensor illustrated in FIG. 1, the paste is printed on the Ni-NiO layer formed on an insulating substrate such as of alumina, dried and sintered, followed by repeating the above procedure at least one more time according to the process of the invention. The solid electrolyte layer after drying is sintered at 800° C. to 1500° C.

When, for example, the superposed layer is finally sintered at about 1420° C., the sintering or calcination prior to the final coating and sintering procedure is conducted preferably at a temperature ranging from about 570° C. to about 1140° C. Higher the calcining temperature, the layer becomes more dense, so that the thickness of the layer obtained after repetitions of the coating and calcining procedure at higher temperature becomes greater than that obtained at lower temperature of calcination. In order to make the layer thickness as small as possible without changing the composition of paste and other operating conditions, it is preferred to use the calcining temperature on a lower side.

In a preferred aspect, the paste is applied onto a suitable substrate, dried and calcined at about 570° C. to about 1140° C., repeating the above procedure, and then the paste is further applied onto the thus treated substrate, dried and sintered at 570° C. to 1140° C. In the best mode of the process of the invention using the solid electrolyte paste, the paste of a powder having a suitable average size of $0.5\mu$ to $8\mu$ (passed through a 400 mesh sieve) is applied onto a suitable substrate, dried and calcined at about 570° C. to about 1140° C., repeating the above procedure one more time, and a paste using a powder of the same type used above but having an average size not greater than 0.9 times that of the firstly and secondly employed powder is applied onto the superposed layer, dried and sintered at about 1420° C.

Aside from the solid electrolyte paste, the process of the present invention is applicable to various types of solid powder-containing pastes ordinarily employed for the production of electronic parts. For example, the process is effectively used to form an insulating layer from alumina or glass insulating pastes which are often applied during the course of fabrication of circuits such as IC for insulation of conductive portion, ensuring formation of a very dense thin layer which is much more improved in dielectric strength, lifetime, and quality as compared with those obtained by the known screen printing method. Further, there can be applied by the process of the invention other known pastes ordinarily used in electronic or electric industry and including, for example, insulating or circuit-protecting pastes of fine powder of borosilicate glass or crystalline frit in organic vehicle, dielectric pastes for capacitor dispersing strongly dielectric barium titanate powder in organic vehicle, resistor pastes such as mixtures of ruthenium oxide and metal powder dispersed in organic vehicle, and conductor pastes used to electrically interconnect two or more elements therewith and containing powders of platinum or its alloys, gold or its alloys, silver or its alloys, or palladium alloys dispersed in organic vehicle. In these pastes, similar organic vehicles as used for the solid electrolyte paste are used. These known pastes are not necessary to be specifically formulated for application by the process of the invention except that a solid powder used in the final coating step is preferred to be smaller in average size as discussed.

The number of repetitions of the coating-sintering or calcining procedure prior to the final coating-sintering procedure varies depending on the type of paste. It has been found that with the solid electrolyte paste, for example, when x=2 or the total number of repetitions is two, the yield of product reaches 98%. When x=3 for alumina insulating paste and x=2 for glass paste, the yield of product reaches approximately 100% in each case. From the above, it is believed that the total number of repetitions of the coating-sintering procedure is sufficient to be within several times.

It should be emphasized here that though it may be considered that the process of the invention is mere repetitions of known screen printing and sintering procedure, the process is very advantageous in an industrial point of view in that a very dense layer is obtained and that such severe controls in preparation of powder and paste, viscosity of the paste, and drying and sintering conditions as will be experienced in known screen printing techniques are not necessary.

The present invention will be particularly illustrated by way of the following examples.

EXAMPLE 1

Solid electrolyte pastes 1 and 2 each having the following formulation were prepared using a solid electrolyte powder with different average sizes.

| Paste 1 | | |
|---|---|---|
| Powder | $ZrO_2$—8 wt % $Y_2O_3$ | |
| Average | about 7.2$\mu$ (passed through a 40 mesh sieve) | |
| Organic vehicle | ethyl cellulose | 6.8 wt % |
| | terpineol | 60.0 wt % |
| | dibutyl phthalate | 32.0 wt % |
| | polyethylene glycol ester | 1.2 wt % |
| Powder content | 50 wt % | |
| Paste 2 | | |
| Powder | $ZrO_2$—8 wt % $Y_2O_3$ | |
| Average | about 6$\mu$ (passed through a 400 mesh sieve) | |
| Organic vehicle | ethyl cellulose | 6.8 wt % |
| | terpineol | 60.0 wt % |
| | dibutyl phthalate | 32.0 wt % |
| | polyethylene glycol ester | 1.2 wt % |
| Powder content (in paste) | 50 wt % | |

The pastes were printed on an alumina substrate by a screen printing method and sintered under conditions indicated below. The resulting solid electrolyte layers were assessed by measuring their water absorption and specific resistance. It is well known that the specific resistance increases with an increased porosity and thus the denseness of layer can be evaluated by comparison of the specific resistances.

Four different types of specimens were made, each type including 20 specimens, according to known procedures A and B and to procedures C and D of the present invention, and were subjected to measurements of water absorption and specific resistance, with the measured values being, respectively, averaged for each type.

Procedure A

The paste 1 was applied once and sintered at 1420° C.

Procedure B

The paste 2 was applied once and sintered at 1420° C.

Procedure

The procedure of application of the paste 1 and calcination at 1000° C. was repeated twice and then the paste 1 was applied onto the repeatedly treated substrate and sintered at 1420° C.

Procedure D

The procedure of application of the paste 1 and calcination at 1000° C. was repeated twice and then the paste 2 was applied onto the repeatedly treated substrate and sintered at 1420° C.

Figure 2:
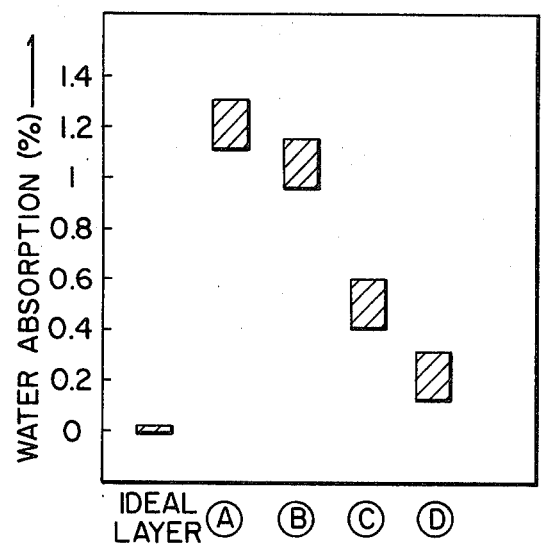
FIG. 2 is a graphical representation of water absorption of two different types of solid electrolyte layers formed according to prior art procedures A and B and of those formed according to procedures C and D of the present invention.

The results of the measurements for the specimens of the respective types are shown in FIGS. 2 and 3 showing the absorption rate and specific resistance, respectively.

From the results, it will be appreciated that the process of the invention can remarkably improve the absorptivity and specific resistance over the known method.

EXAMPLE 2

An oxygen sensor of the construction shown in FIG. 1 was made using an solid electrolyte layer formed according to the procedure D of Example 1 and subjected to a measurement of output characteristic. For comparison, an oxygen sensor using a solid electrolyte layer formed by the procedure A of Example 1 and was similarly measured to determine its output characteristic. The results are shown in FIG. 4.

From the figure, it will be seen that the oxygen sensor using the solid electrolyte layer formed by the procedure D of the invention is very stable in output voltage. On the other hand, the sensor using the electrolyte layer formed by the known procedure A is considerably lowered in output voltage and is thus unfit as a sensor for controlling a combustion system of automotive engines.

EXAMPLE 3

Alumina insulating pastes 1 and 2 having the following formalation were prepared using an insulating powder with different average sizes.

| Paste 1 | | |
|---|---|---|
| Powder | $Al_2O_3$ | |
| Average | 2.0$\mu$ (maximum ... 10.0$\mu$) | |
| Organic vehicle | ethyl cellulose | 8.4 wt % |
| | terpineol | 79.0 wt % |
| | dibutyl phthalate | 10.0 wt % |
| | polyethylene glycol ester | 1.6 wt % |
| Powder content (in paste) | 50 wt % | |
| Paste 2 | | |
| Powder | $Al_2O_3$ | |
| Average | 1.6$\mu$ (maximum ... 10.0$\mu$) | |
| Organic vehicle | ethyl cellulose | 8.4 wt % |
| | terpineol | 79.0 wt % |
| | dibutyl phthalate | 10.0 wt % |
| | polyethylene glycol ester | 1.6 wt % |
| Powder content (in paste) | 50 wt % | |

Specimens were prepared using the pastes 1 and 2 as follows: A paste containing platinum is printed onto an alumina substrate and then was sintered at about 1200° C. The alumina insulating paste 1 was printed onto the paste containing platinum and then was calcined at about 910° C. Such printing of the alumina insulating plaste and its calcination were repeated one more time. Thereafter, the alumina insulating paste 2 was printed onto the formed layer of the paste 1 and then sintered at about 1300° C. Further, a paste containing platinum was printed onto the thus formed layer of the paste 2 and then sintered at about 1200° C.

The specimens obtained by the above-mentioned method were assessed by measuring electrical insulation effect between the upper and lower platinum electodes which were formed in the above-mentioned manner using the pastes containing platinum, respectively. As a result, 192 specimens in 200 specimens exhibited good electrical insulation, without causing "short".

For reference, the electrical insulation effect was measured with respect to the specimens prepared by a conventional method in which the insulating layer was formed by only one time sintering using the above-mentioned insulating paste 2. As a result, only about 60 to 70% of all the specimens exhibited good electrical insulation. It will be appreciated from such results, that the insulating layer formed according to the present invention is excellent as compared with that formed according to conventional methods.

While only Alumina ($Al_2O_3$) has been described as used as the powder contained in the alumina insulating pastes 1 and 2 in Example 3, it will be appreciated that a mixture of alumina and Silica ($SiO_2$) or Magnesia (MgO) may be used as the same powder.

What is claimed is:

1. A process for forming a thin dense oxygen ion conductive solid electrolyte layer from a solid electrolyte paste of oxygen ion conductive solid electrolyte powder in an organic vehicle, said process comprising the steps, in the following order, of:
    applying a solid electrolyte paste of $Y_2O_3$-$ZrO_2$ onto a substrate by a screen printing technique, and sintering said applied paste under sintering conditions; and
    repeating at least one more time the above procedure of applying a paste of the same material as the initially applied paste onto said substrate provided with the sintered paste, and sintering the repeated application of paste under sintering conditions;
    the sintering of the final application of paste being effected at a temperature of about 1420 degrees C., and the sintering of each application of paste prior to the final application of paste being effected at a temperature of 0.4 to 0.8 times the temperature used to sinter the final application of paste.

2. A process according to claim 1, wherein the paste is a glass paste and the procedure is repeated three times.

3. A process according to claim 1, wherein when the procedure is repeated at least three times.

4. A process according to claim 3, wherein each applied paste is calcined at about 570° C. to about 1140° C. and the final sintering is conducted at about 1420° C.

5. A process according to claim 1, wherein the powder has an average size of $0.5\mu$ to $8\mu$, and a maximum size of $40\mu$ or less.

6. A process according to claim 4, wherein the paste is applied onto the substrate, dried and calcined at about 570° C. to about 1140° C., repeating the procedure two times, and the paste is further applied onto the thus treated substrate, dried and sintered at about 1420° C.

7. A process according to claim 1, wherein a paste containing $Y_2O_3$-$ZrO_2$ is applied onto the substrate, dried and calcined at about 570° C. to about 1140° C., repeating the procedure one more time, and a paste comprising a powder of the same material having an average size not greater than 0.9 times that of the firstly and secondly employed powder is applied onto the superposed layers, dried and sintered at about 1420° C.

8. A process for forming a thin dense oxygen ion conductive solid electrolyte layer from a solid electrolyte paste of oxygen ion conductive solid electrolyte powder in an organic vehicle, said process comprising the steps, in the following order, of:
    applying a solid electrolyte paste of $Y_2O_3$-$ZrO_2$ onto a substrate by a screen printing technique, and sintering said applied paste under sintering conditions; and
    repeating at least one more time the above procedure of applying a paste of the same material as the initially applied paste onto said substrate provided with the sintered paste, and sintering the repeated application of paste under sintering conditions;
    the sintering of the final application of paste being effected at a temperature of about 1420 degrees C., and the sintering of each application of paste prior to the final application of paste being effected at a temperature of 0.4 to 0.8 times the temperature used to sinter the final application of paste;
    the powder in the paste used in the final application of paste having an average size not greater than 0.9 times the average size of the powder in the paste used in the initial application of paste.

* * * * *